United States Patent
Benje

(10) Patent No.: US 6,191,329 B1
(45) Date of Patent: Feb. 20, 2001

(54) PROCESS FOR SPECIFIC ENERGY SAVING, ESPECIALLY IN THE OXYCHLORINATION OF ETHYLENE

(75) Inventor: Michael Benje, Darnstadt (DE)

(73) Assignee: Krupp Uhde GmbH, Dortmund (DE)

( * ) Notice: Under 35 U.S.C. 154(b), the term of this patent shall be extended for 0 days.

(21) Appl. No.: 09/363,759

(22) Filed: Jul. 29, 1999

(30) Foreign Application Priority Data

Jul. 27, 1999 (DE) .............................................. 198 34 083

(51) Int. Cl.$^7$ ...................................................... C07C 17/15
(52) U.S. Cl. ........................ 570/243; 570/224; 570/244; 570/245
(58) Field of Search ................................... 570/224, 243, 570/244, 245

(56) References Cited

U.S. PATENT DOCUMENTS 3,987,119 * 10/1976 Kurtz et al. .
4,042,639 * 8/1977 Gorden et al. .

* cited by examiner

*Primary Examiner*—Alan Siegel
(74) *Attorney, Agent, or Firm*—Rosenman & Colin, LLP

(57) ABSTRACT

A process for specific energy saving, especially in processes involving the oxychlorination of ethylene, facilitates recovery of as much sensible heat to be used for other purposes. In the process the gas mixture leaving the oxychlorination reactor is cooled before it enters the quenching column and the heat recovered is then used to preheat the ethylene recycle gas feed stream.

6 Claims, 2 Drawing Sheets

PROCESS FOR SPECIFIC ENERGY SAVING, ESPECIALLY IN THE OXYCHLORINATION OF ETHYLENE

FIELD OF THE INVENTION

The invention is generally directed to saving energy, particularly during oxychlorination processes.

BACKGROUND OF THE INVENTION

It is known that the reaction mixture at the outlet of an oxychlorination reactor mainly comprises the EDC (1,2-dichloroethane), water gas and recycling gas (carbon dioxide, nitrogen, argon) and has a temperature of 220° C. at a pressure of approx. 4.2 bar. Because friction occurs in the catalyst, the stream leaving the reactor is passed through a micron filter to catch the dust discharged by the catalyst and/or through a cyclone and is then fed into the quenching column. The column is used for washing the hydrogen chloride out of the reactor discharge stream and for neutralizing it and for promoting the alkaline decomposition of chlorinated by-products, such as chloral.

Sensible heat is withdrawn from the reaction mixture in the quenching column. The temperature at the head of the column is 102' C. The reaction products., water and EDC, are condensed in the raw EDC condenser downstream of the column before being individually separated and removed from the recycling gas in an EDC settling vessel. The water obtained and the caustic soda (which serves to neutralize and decompose by-products) are fed back to the quenching column as reflux at a temperature of approx. 400C. A part-stream, approximately equal in volume to that of the reaction water, is drawn off at the bottom of the quenching column and fed to a waste water treatment stage.

A sufficient quantity of liquid must be constantly supplied to the quenching column to ensure that it functions correctly. The column discharge can be split into two constituents: one being the reaction water which enters the column with the reactor discharge stream prior to being condensed in the raw-EDC condenser; the other being the water from the column, which is evaporated using some of the sensible heat from the reactor discharge stream before being condensed in the raw-EDC condenser.

This last constituent is thus in constant circulation as a result of the continuous evaporation and subsequent condensation processes- most of the sensible heat at the reactor outlet is dissipated by cooling water.

SUMMARY OF THE INVENTION

The invention is applied at this stage. Its aim is to recover as much heat as possible to enable as much sensible heat from the oxychlorination reactor as possible to be used for other purposes. A process of the type described above meets this requirement by cooling the gas mixture leaving the oxychlorination reactor before it enters the quenching column. The heat produced is then used to preheat the ethylene recycled gas feed stream.

The invention permits the creation of quench reflux and the cooling of the reactor discharge stream to be carried out separately. Consequently, most of the sensible heat at the outlet of the oxychlorination reactor can be used for other purposes, One other particular advantage of the invention is that the condensation system at the quenching column head can be designed for lower throughputs which ultimately results in reduction in costs.

To enable the heat potential from the gas mixture leaving the oxychlorination reactor to be fully utilized, one embodiment of the invention provides for the gas mixture to be cooled to a temperature just above its dew point, the latter being influenced by the reaction water content.

This ensures that most of the reaction water formed in the oxychlorination reactor is fed into the quenching column as steam and can then be drawn off at the head of the quenching column in the form of steam together with the EDC. It is then condensed and separated in the settling vessel so that it can be used as the aqueous quench reflux required. If this were not the case and the dew point were not reached, some of the reaction water would trickle directly into the bottom of the quenching column in liquid form. This would then lead to increased caustic soda consumption to maintain the required pH level in the bottom of the quenching column.

If the gas mixture can be cooled using a single-pass heat exchanger with co-current flow, the outlet temperature of the gas mixture should be brought so close to the dew point that a temperature difference of only 5K remains. Practical experience has shown this to be the acceptable limit value for ensuring a stable process operation.

The present invention is certainly not limited for use exclusively with outlet temperatures above the dew point. For example, an alteration to the reaction flow in the oxychlorination reactor can lead to reduced caustic soda requirements, which could in turn cause a part-stream of the reaction water, which has liquefied due to the dew point not being reached, to trickle directly into the quenching water vessel.

Further embodiments of the process according to the invention can be seen in the dependent claims.

BRIEF DESCRIPTION OF THE DRAWINGS

Other advantages, details and characteristics of the invention are contained in the following Detailed Description of the Preferred Embodiment and in the figures, in which.

DETAILED DESCRIPTION OF THE PREFERRED EMBODIMENT

Figure 1:
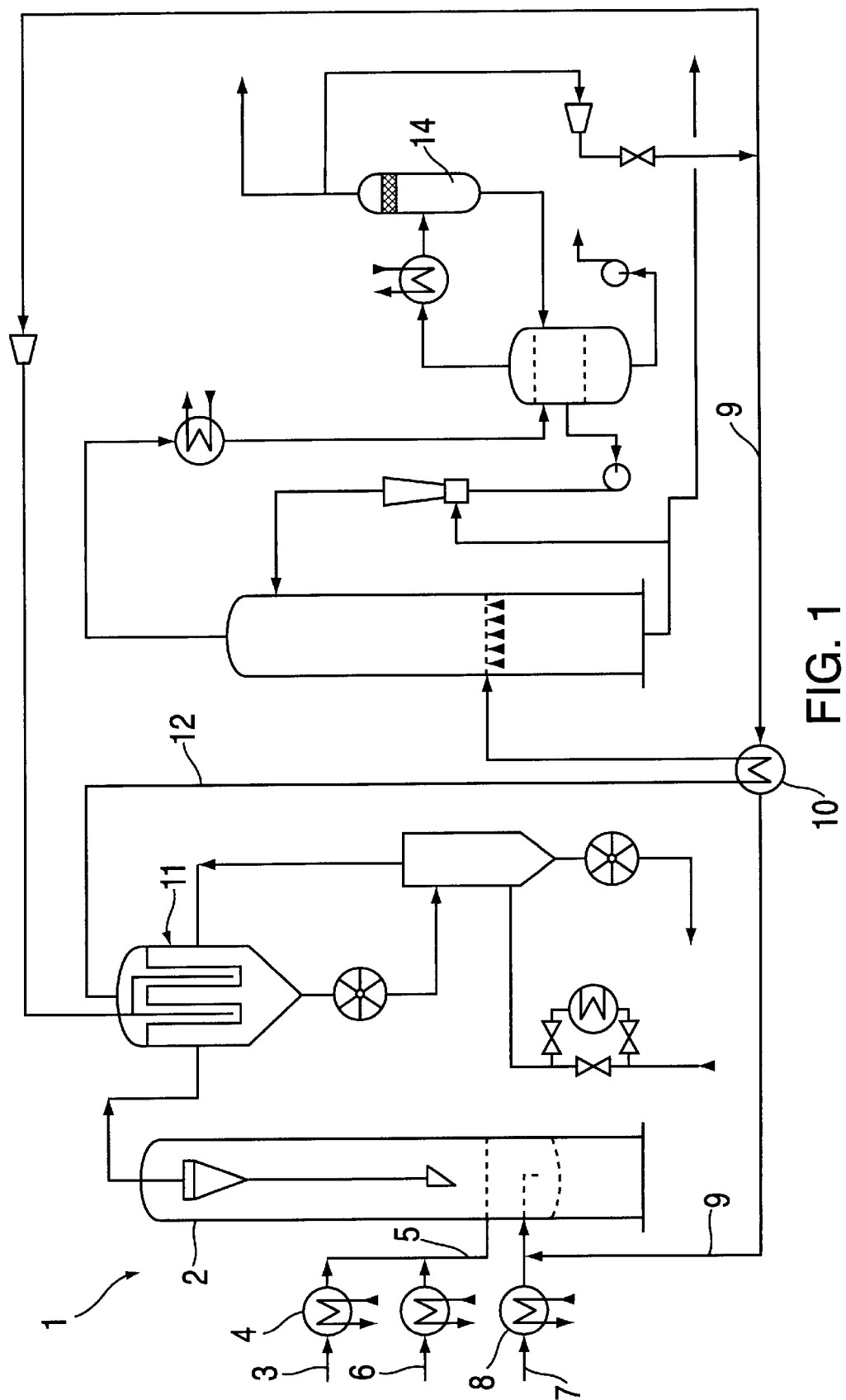
FIG. 1 is a process plant layout in accordance with the invention.

Referring now to the drawings, FIG. 1 shows a plant I having a reactor 2, which is supplied via line 5 with hydrochlorine coming from lines 3 which have preheaters 4. Oxygen is supplied to the reactor 2 via line 6 and ethylene is supplied via line 7 and the preheater 8. The gas phase is fed back to the reactor 2 along line 9 and passes through the heat exchanger 10 which is supplied with a raw 1,2-dichloroethane gas stream from the head of the cyclone via line 12.

Figure 2:
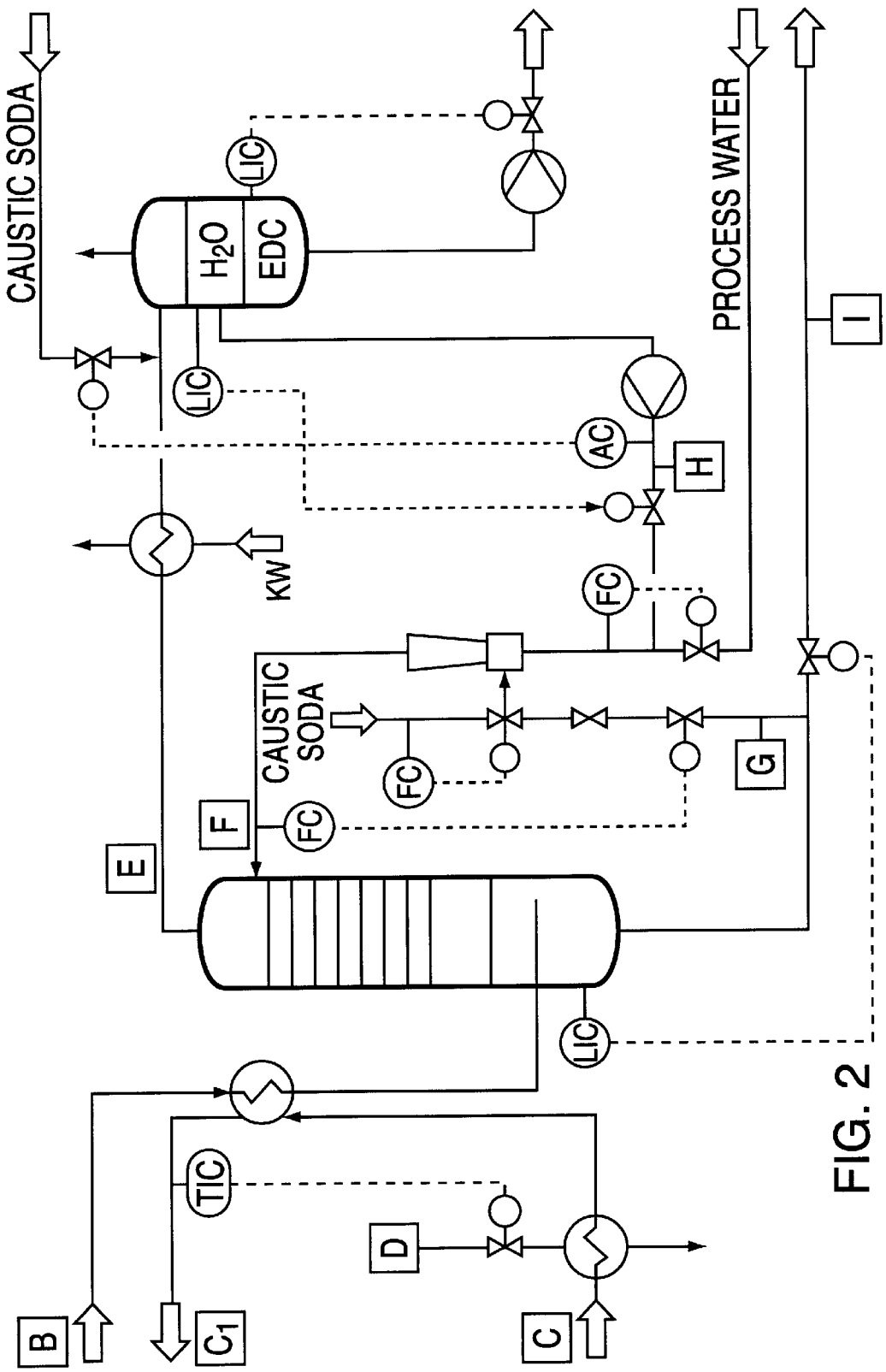
FIG. 2 is a slightly modified process plant layout with reference made to the parameters required for a configuration as described below.

FIG. 2 shows the configuration in which the discharge from the quenching column bottom can be added via an ejector pump 13 which is fed by the water phase from the raw-EDC settling vessel. In FIG. 2, the capital letters in the squares refer to typical process parameters as given below.

Heat Balance for Oxyquenching with Feed-side Preheating

A: 43561 kg/h
3128 kg/h
$H_2O$ T=160° C.
$\Delta H(160 \rightarrow 101°$ C.$) \sim 750$ kW B: Oxyreactor outlet
  43530 kg/h
  T=220° C.
  p≈4.2 bar a
C: Ethylene recycled gas
  T≈57° C.
  p≈6.2 bar a
  C1 ethylene recycle gas T≈150° C.
  p≈6 bar a
D: Steam
  10 bar a 180° C.
E: 44329 kg/h
  2896 kg/h $H_2O$
  T≈101° C.
F: 5155 kg/h
  5089 kg/h $H_2O$
  T≈56° C.
G: 1259 kg/h
  T≈105° C.
H: 3896 kg/h $H_2O$
  T≈40° C.
I: 3347 kg/h
  T≈105° C.

As can be seen from FIG. 2 and from the above numbers, the reactor discharge stream is cooled to 160° C. in a single-pass heat exchanger and is, as a result, still above the dew point. The feed stream in this particular configuration is heated to 150° C.

The temperature of the quenching column head stream is still 101° C., but in this case less water is evaporated in the column. This leads to the throughput of the condenser at the quenching column head being reduced by approximately 12%. To ensure that sufficient quench reflux is maintained, some of the part-stream withdrawn from the quenching column bottom is admixed with the water phase from the raw-EDC settling vessel. The water phase from the raw-EDC settling vessel can be used as a jet stream by utilizing an ejector pump. A flow controller initiates the addition of process water to keep this jet constant in the event of fluctuations. The entire volume of reflux is regulated by intake stream circulation controlled by another flow meter. As can be seen in FIG. 2, a fixed amount of caustic soda is added to the intake stream. The quenching column bottom can thus be operated in any pH range.

The examples covered in FIG. 2 and in the above table result in a considerable saving on operating costs.

While the preferred embodiment of the invention has been disclosed in detail, modifications and adaptations may be made thereto without departing from the spirit and scope of the invention as delineated in the following claims:

What is claimed is:

1. A method for specific energy saving in the oxychlorination of ethylene, said method comprising the steps of:
   initially cooling the gas mixture leaving an oxychlorination reactor;
   allowing the cooled gas to enter a quenching column; and
   using heat transmitted in the above steps to preheat the feed stream of a mixture of ethylene and recycle gas.

2. The method of claim 1, wherein the cooling step the gas mixture leaving the oxychorination reactor is cooled to a temperature just above the dew point before it enters the quenching column.

3. The method of claim 1, further providing the step of recycling quench bottom stream to a top of the quenching column.

4. The method of claim 3, further providing the step of mixing the quench bottom stream with condensed reaction water.

5. The method of claim 3, further providing the step of admixing the quench bottom stream via one of a plurality of ejector pumps driven by condensed reaction water.

6. The method of claim 3, further providing caustic soda to the quench bottom stream.

* * * * *